United States Patent [19]

Boehmer et al.

[11] Patent Number: 4,726,382
[45] Date of Patent: Feb. 23, 1988

[54] INFLATABLE FINGER CUFF

[75] Inventors: Robert D. Boehmer, Englewood, Colo.; Arthur A. Pratt, Madison; Kenneth J. Kuehl, Oregon, both of Wis.

[73] Assignee: The BOC Group, Inc., Montvale, N.J.

[21] Appl. No.: 908,461

[22] Filed: Sep. 17, 1986

[51] Int. Cl.⁴ .............................................. A61B 5/02
[52] U.S. Cl. .................................... 128/667; 128/686
[58] Field of Search ............................. 128/664–667, 128/672, 677, 686, 327

[56] References Cited

U.S. PATENT DOCUMENTS

| | | |
|---|---|---|
| 3,467,077 | 9/1969 | Cohen . |
| 3,765,405 | 10/1973 | Natkanski . |
| 4,038,976 | 8/1977 | Hardy et al. . |
| 4,091,803 | 5/1978 | Pinder ................................ 128/666 |
| 4,406,289 | 9/1983 | Wesseling et al. ............. 128/672 X |
| 4,593,692 | 6/1986 | Flowers .......................... 128/686 X |
| 4,597,393 | 7/1986 | Yamakoshi et al. ............ 128/667 X |
| 4,605,010 | 8/1986 | McEwen ............................. 128/686 |

FOREIGN PATENT DOCUMENTS 1906346 8/1970 Fed. Rep. of Germany ...... 128/686
8005144 9/1980 Netherlands .

OTHER PUBLICATIONS

Hammer et al.; "Indirect Blood Pressure Finger Cuff", *IBM* Technical Disclosure Bulletin, vol. 8, No. 4, 9–1965.

Primary Examiner—William E. Kamm
Assistant Examiner—Angela D. Sykes
Attorney, Agent, or Firm—Roger M. Rathbun; Larry L. Cassett

[57] ABSTRACT

An inflatable cuff is disclosed for encircling a patient's finger and which includes a light source and a light detector constructed in a way to detect the movement, or lack of movement, of arterial passages within the finger. The cuff is comprised of an inflatable bladder that contacts the patient finger; having a tubing provided for inflation and deflation of the bladder. Surrounding the external surface of the bladder from the finger is a metalized backing that covers and shields the inflatable bladder. A flexible circuit is affixed to the metalized backing and to which is attached the light source and light detector and which further includes wiring from the light detector and light source to a connector at its distal end for connection to further circuiting. Further, surrounding the flexible circuit is a electrical and light shielding and label that covers the flexible circuit and which provides shielding as well as a means of affixing the inflatable cuff to the patients finger. The overall cuff is readily manufacturable and particularly adapted for its specialized use.

13 Claims, 4 Drawing Figures

INFLATABLE FINGER CUFF

BACKGROUND OF THE INVENTION

This invention relates to an inflatable cuff for use with an instrument for determining the blood pressure of a patient.

Certainly the most used instrument for measuring a patient's systolic and diastolic blood pressure is the sphygmomanometer. That device utilizes a flexible cuff that encircles, typically, a patient's arm and which is thus inflated to increase its pressure to cause changes in the flow of blood within the arterial passages in the patient's arm. By raising that pressure in excess of the patient's systolic pressure and thereafter gradually reducing the cuff pressure, determinations are readily made of the systolic and diastolic pressures.

Other apparatus has, however, been developed, typical of which is disclosed in U.S. Pat. No. 4,406,289, and which makes the measurement of a patient's blood pressure by use of arterial passages in a patient's digit, preferably a finger, rather than the arm. Such apparatus is, under certain conditions, less cumbersome to use and, of course, may be used where access to the patient's arm is difficult or would impede ongoing surgical operations. As noted in U.S. Pat. No. 4,406,289, the finger cuff can also be used with certain specialized apparatus to obtain blood pressure readings on a continuous basis.

It is, therefore, desirable to provide a flexible, inflatable cuff that is designed to encircle a patient's finger, rather than the arm, and which includes, not only an inflatable means to control blood flow in the finger, but a light source and a light detector to carry out the functions described in the aforementioned U.S. Patent.

Certainly it is further desirable that such a cuff be readily manufacturable on a low-cost basis in relatively large quantities of uniform specifications and quality.

Present finger cuffs have been used to detect pulse and other functions that use LED's and light detectors; however, the present inflatable cuff is commercially reproducible in large quanities with relatively inexpensive manufacturing costs and which are made with sufficient consistency as to have similar characteristics so as to be readily replaceable.

SUMMARY OF THE INVENTION

In accordance with the invention, a finger cuff is provided that is readily manufacturable at relatively low cost in volume production.

The cuff is basically formed of separate components that are adhesively joined together to form an inflatable cuff adapted to encircle a patient's finger and which further includes a light source and light detector positioned with respect to each other as to pass and receive light through the finger. An outer wrapper of the cuff provides the necessary labeling and also provides a means to retain the cuff about the finger.

Specifically, the cuff in its preferred embodiment, comprises an inflatable bladder formed of a thin flexible, translucent material and which has a tube extending therefrom to carry out the inflation and deflation of the bladder. The bladder is the innermost component of the cuff as it fits about the patient's finger. An aluminized coating covers the inflatable bladder by an adhesive bonding. The aluminized coating is a reflective, opaque surface and physically covers the inflatable bladder on its surface away from the patient's finger. The aluminized coating serves as an electrical shield as well as a light reflector, the purpose of which will become apparent. In addition, in manufacturing the inflatable bladder, openings are provided for later positioning of the light source and light detector to penetrate the bladder so as to directly contact the finger, and similar openings are therefore provided in the aluminized coating.

A flexible circuit thereafter is affixed to and covers the outer aluminized coating. The surface that faces the aluminized coating is of an insulating material, preferably polyimide and also provides conductive pads for hard wiring connections to the light source and light detector as they are mounted to the polyimide side of the flexible circuit. The outer surface of the flexible circuit is a conductive metalized surface, preferably copper, that proves shielding from external electrical and/or light interference. Additional conductive metalized layers may cover the outer conductive metalized surface of the flexible circuit for additional shielding. As used herein, the proximal end of the inflatable finger cuff means the end extending towards the patient's arm, and the distal end is the furthermost end of the cuff at the extremity of the patient's finger. The flexible circuit is dimensionally manufactured such that the light source and light detector align with the openings in the bladder where those two components are mounted on the flexible circuit and surround a patient's finger.

Finally, a flexible cover overlies the conductive metalized surface and is adhesively affixed thereto. The cover includes the necessary labeling and indicia for properly installing the finished cuff about a patient's finger. An adhesively coated flap on the cuff may be used to overlap the flexible cover when placed on the patient's finger to retain the cuff encircling the finger.

DESCRIPTION OF THE PREFERRED EMBODIMENT

Figure 1:
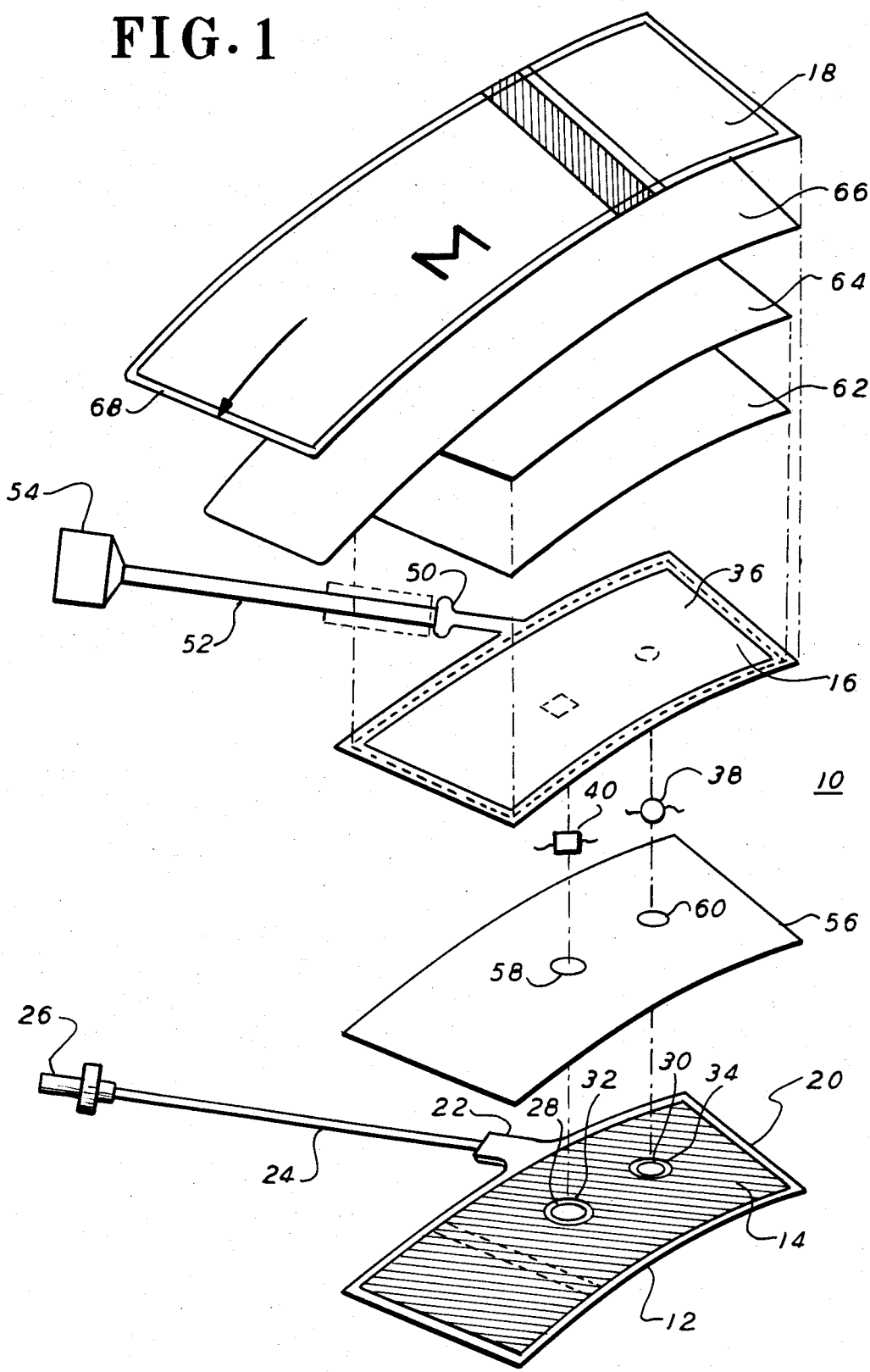
FIG. 1 is an exploded view showing the basic components which, when assembled, make up the inflatable cuff of the present invention.
Figure 2:
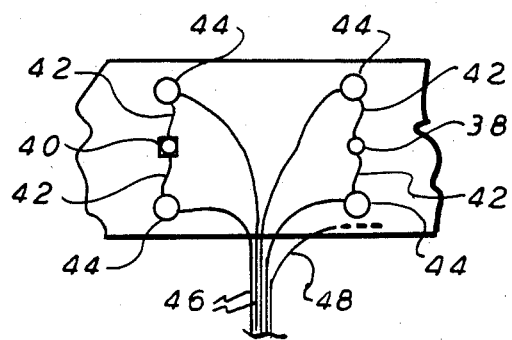
FIG. 2 is an enlarged, cut away view of the inner surface of one of the cuff components showing the means of attaching a light emitter and light detector used in accordance with the present invention.

Referring now to FIGS. 1 and 2, there is shown an inflatable cuff 10 constructed in accordance with the present invention. In the exploded view of FIG. 1, the basic main components of the inflatable cuff 10 comprise an inflatable bladder 12 with a metalized layer 14 covering the inflatable bladder 12, a flexible circuit 16 carrying the electrical conductors and a cuff label 18 that forms the outer cover for the inflatable cuff 10.

Taking the construction of the components individually, inflatable bladder 12 is comprised of a flexible translucent material having an inflatable chamber 20 formed therein that is adapted to be inflated by a source of external fluid (preferably gas) at predetermined pressure and, of course, selectively deflated. In the preferred embodiment, inflatable bladder 12 comprises two pieces of material such as urethane film of the same general dimensions and which are heat sealed together about their periphery forming there between an inflatable chamber 20. For purposes of its use in the system of U.S. Pat. No. 4,406,289, it is advantageous for the urethane film that faces the patient's finger in use to be thinner than the outer urethane film, preferably the inner urethane film has a thickness of about 1–2 mils and the outer urethane film a thickness of 5–7 mils. Other flexible materials may be used, however, the material is preferably translucent to light and should be relatively tough and abrasion resistant.

An opening 22 is formed in the inflatable bladder 12 and to which is sealed one end of a tube 24 having at its other end, a fitting 26 for connection to a source of gas or other fluid for inflating and deflating the inflatable bladder 12. The tube 24 is also of a flexible material such as urethane and can be RF heat sealed to opening 22.

Openings 28 and 30 are formed in inflatable bladder 12 and are aligned and of a particular geometric configuration to conform to the dimensions and spacing of a light source and a light detector as will be later explained.

A metalized layer 14 is provided and which covers the outer surface of inflatable bladder 12. The metalized layer 14 is an aluminized layer in the preferred form, however, other conductive, reflective metals can be used that are capable of acting as light reflectors and electrical shields. As used hereinafter, the reference to inner surfaces indicates those surfaces facing the patient's finger when inflatable cuff 10 is installed surrounding that finger. Outer surfaces, therefore, refer to those surfaces facing away from the patient's finger when so installed.

Openings 32 and 34 are formed in metalized layer 14 aligned with openings 28 and 30 of inflatable bladder 12.

Flexible circuit 16 is constructed of a non-conductive material but having a conductive coating on its outer surface. Preferably, flexible circuit 16 is made of polyimide approximately 3 mils. in thickness and having a copper tinned outer surface 36 of approximately 1.4 mils.

A light source 38 and light detector 40 are both mounted to the inner surface of flexible circuit 16 by connection thereto through electrical wiring. When mounted, each are surrounded by an adhesive sealant having an opaque consistency to prevent light piping. A typical sealant is available commercially as a silastic brand adhesive brand sealant of Dow Chemical Company. The sealant additionally protects light-source 38 and light detector 40 against fluids or other contamination.

In FIG. 2, there is shown the lower surface of flexible circuit 16 and to which have been affixed four solder pads 44 by an adhesive. As may be seen, the light source 38 and light detector 40 have electrical leads (all indicated collectively by the number 42) and which run from those components to the solder pads 44 where they are electrically connected and which connections hold the light source 38 and light detector 40 in place on the flexible circuit 16. Additional component wires 46 are thus also electrically connected to each of the solder pads 44 and provide external connections. An additional ground wire 48 is electrically connected to the copper outer surface 36 of the flexible circuit 16.

Returning to FIG. 1, all of the component wires 46 and the ground wire 48 are encased in insulating material formed into a strain relief 50 to multi wire cable 52 to a connector 54 at its distal end that is adapted to connect, either directly or indirectly, to the electronic circuitry used with the blood pressure monitoring equipment.

Flexible circuit 16 is adhered to the outer surface of the inflatable bladder 12, by means such as a double sided adhesive coated mylar strip 56 and which covers entirely the metalized layer 14 of inflatable bladder 12, thus providing an adhesive as well as electrical insulation. Mylar strip 56 also has two holes 58 and 60 so that light source 38 and light detector 40 can operate directly upon the patient's finger.

Light source 38 may be of conventional commercially available LED's and light detector 40 also of conventional make and readily available commercially to detect the particular wavelength of light emitted by light source 38.

The outer copper surface of flex circuit 16 provides electrical shielding to the inflatable cuff and may be a single relatively thick copper coating or preferable, as shown, additional thinner copper layers 62 and 64 can be used to allow better flexibility while still providing electrical shielding.

As shown, the additional copper layer 62 and 64 are affixed together, and to the copper outer surface 36 of flexible circuit 18 by an electrically conducting adhesive.

Cuff label 18 is the outermost component of inflatable cuff 10 and provides, on its outer surface, various printed indicia such as instructions for use, labeling and the like. The cuff label 18 is opaque and may have an adhesively coated inner surface to adhere to the copper layer 64, or as shown, may be affixed by a double sided adhesive coated mylar strip 66.

As noted, a flap 68 extends beyond the surface area of flexible circuit 16 and is left free to overlap and seal against itself when inflatable cuff 10 encircles the finger of a patient.

Figure 3:
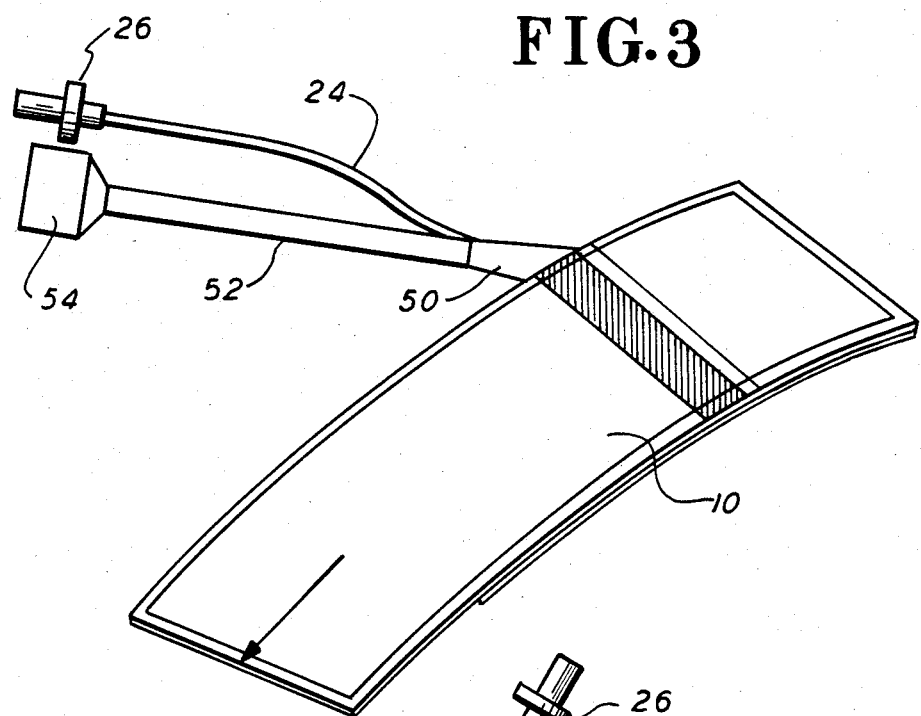
FIG. 3 is a perspective view of the inflatable cuff of FIG. 1 shown in its completed form.
Figure 4:
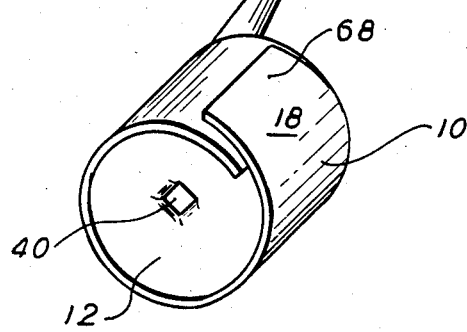
FIG. 4 is a perspective view of the inflatable cuff of FIG. 1 shown in its as used condition.

Turning now to FIGS. 3 and 4, the inflatable cuff 10 is shown in perspective in its completed form in FIG. 3 and in FIG. 4 in its operative position normally encircling a patient's finger. In FIG. 4, it can be seen that the inner surface of the inflatable bladder 12 thus contacts the finger directly and is inflatable by suitable means through the tube 24.

The light detector 40 is shown and which contacts the finger and which receives light from light source 38 (not shown in FIG. 4). The light source 38 however locates itself in affixing the inflatable cuff 10 to the patient's finger generally opposite the light detector 40 so that light passes directly through the finger from light source 38 to light detector 40.

Inflatable cuff 10 is readily mounted to the patient finger by encircling that finger by the flap 68 that overlaps sufficient of the outer surface of cuff label 18 to adhere thereto by the adhesive inner surface of cuff label 18 to hold inflatable cuff 10 securely in position. Outer cuff label 18 is sufficienltly unstretchable so as to allow inflation of the inflatable bladder 12 to affect circulation of blood within the arterial system of the patients finger.

Having set forth the invention in what is considered to be the best embodiment thereof, it will be understood that changes may be made in the inflatable cuff and the method of making the same without departing from the spirit of the invention or exceeding the scope thereof as defined in the following claims.

We claim:

1. An inflatable cuff for encircling the digit of a patient, said inflatable cuff comprising: an inflatable bladder adapted to encircle the digit and be inflatable and deflatable to effect flow of blood within the digit, a flexible circuit substantially surrounding said inflatable bladder, said flexible circuit having electrical connection means, a light detector and light emitter affixed electrically to said electrical connection means, electrical wires connected to said electrical connection means and having free ends for connection to an external source of electricity, said light emitter positioned to direct light through said digit to said light detector, reflecting means surrounding said digit and adapted to reflect light diffused from the digit back toward the digit, shielding means substantially surrounding said light emitter and said light detector preventing extraneous electrical interference from affecting said light emitter and said light detector, label means surrounding and adhered to said flexible circuit, said label means having a free end adapted to wrap more than 360° around said digit to overlap and adhere said free end to said overlapped label to retain said inflatable cuff encircling the digit.

2. An inflatable cuff as defined in claim 1 wherein said inflatable bladder is a thin, flexible translucent material and includes a tube extending therefrom for inflating and deflating said bladder.

3. An inflatable cuff as defined in claim 2 wherein said inflatable bladder has a pair of openings adapted to align with said light emitter and light detector to allow said emitter and detector to directly contact the patient's digit.

4. An inflatable cuff as defined in claim 1 wherein said flexible circuit is polyimide and said electrical connection means comprise solder pads.

5. An inflatable cuff for encircling the digit of a patient, said inflatable cuff comprising: an inflatable bladder adapted to encircle the digit and be inflatable and deflatable to effect flow of blood within the digit, a backing substantially surrounding the outer surface of said inflatable bladder, said backing being of a conductive reflective material, a flexible circuit surrounding said backing and adhered thereto, said flexible circuit having an internal surface of non-conductive material and an outer surface of conductive material, electrical connection means on said non-conductive surface of said flexible circuit, a light detector and light emitter affixed electrically to said electrical connection means, electrical wires connected to said electrical connection means and having free ends for connection to an external source of electrically, said light emitter positioned to direct light through said digit to said light detector, shielding means substantially surrounding said light emitter, said light detector and said flexible circuit preventing electrical interference from affecting said light emitter and said light detector, label means having a free end adapted to wrap more than 360° around said digit to overlap and adhere said free end to said overlapped label to retain said inflatable cuff encircling the digit.

6. An inflatable cuff as defined in claim 5 wherein said inflatable bladder is a flexible translucent material having an inner film of about less than 0.005 inches thick and an outer film of about more than 0.005 inches thick.

7. An inflatable cuff as defined in claim 5 wherein said backing substantially surrounding said inflatable bladder comprises a flexible aluminized film adhesively adhered to said bladder.

8. An inflatable cuff as defined in claim 5 wherein said flexible circuit is polyimide and said electrical connection means comprises conductive metallic pads adhesively affixed to said flexible circuit.

9. An inflatable cuff as defined in claim 8 wherein said flexible circuit has its outer surface coated with a conductive metal.

10. An inflatable cuff as defined in claim 5 wherein said shielding means comprises at least one flexible film of a conductive metal.

11. An inflatable cuff as defined in claim 10 wherein said shielding means comprises a plurality of flexible copper films.

12. A method of making an inflatable cuff adapted to encircle a patients digit, said method including the steps of; encircling the patient's digit with an inflatable bladder having an inside surface and an outside surface, adhering a flexible circuit having an inside non-conductive surface and an outside conductive surface to the outside surface of said inflatable bladder, providing electrical connection means on said non-conductive surface of said flexible circuit, mounting a light detector and a light source on said flexible circuit and electrically connecting said light detector and said light source to said electrical connection means in a position such that light from said light source travels through the digit and is detected by said light detector, covering said flexible circuit with a conductive layer of shielding material, and covering said shielding material with an opaque label of sufficient length to wrap more than 360° around the digit to overlap and adhere to itself.

13. A method of making an inflatable cuff adapted to encircle a patient's digit, said method including the steps of: encircling the patient's digit with an inflatable bladder having an inside surface and an outside surface, covering the outside surface of said inflatable bladder with a backing of a conductive reflective material, adhering a flexible circuit having an inside non-conductive surface and an outside conductive surface to the outside surface of said backing, providing electrical connection means on said non-conducting surface of said flexible circuit, mounting a light detector and a light source on said flexible circuit electrically connected to said electrical connection means in positions such that light from said light source travels through the digit and is then detected by said light detector, covering said flexible circuit with a conductive layer of shielding material, and covering said shielding material with an opaque label of sufficient length as to wrap more than 360° around the digit and overlap and adhere to itself.

* * * * *

UNITED STATES PATENT AND TRADEMARK OFFICE
CERTIFICATE OF CORRECTION

PATENT NO. : 4,726,382
DATED : 2/23/88
INVENTOR(S) : Robert D. Boehmer, Arthur A. Pratt and Kenneth H. Kuehl It is certified that error appears in the above-identified patent and that said Letters Patent is hereby corrected as shown below:

Column 5, line 50 "...to an external source of electrically,..." should be "...to an external source of electricity,...".

Signed and Sealed this

Twenty-ninth Day of August, 1989

Attest:

DONALD J. QUIGG

Attesting Officer

Commissioner of Patents and Trademarks